United States Patent [19]
Johnson et al.

[11] Patent Number: 5,885,781
[45] Date of Patent: Mar. 23, 1999

[54] REGULATION OF CYTOKINE SYNTHESIS AND RELEASE

[75] Inventors: Kirk Johnson, Moraga; Abla A. Creasey, Piedmont, both of Calif.; Lucien A. Aarden, Amsterdam, Netherlands

[73] Assignees: Chiron Corporation, Emeryville, Calif.; Central Laboratory of the Netherlands Red Cross Blood Transfusion Service, Amsterdam, Netherlands

[21] Appl. No.: 486,384

[22] Filed: Jun. 7, 1995

[51] Int. Cl.$^6$ .................. G01N 33/53; G01N 33/48; A61K 45/00; A01N 37/18

[52] U.S. Cl. .................. 435/7.1; 424/278.1; 436/63; 514/2

[58] Field of Search .................. 424/9.2, 278.1; 514/2; 435/7.1; 436/63

[56] References Cited

U.S. PATENT DOCUMENTS

| | | | |
|---|---|---|---|
| 5,106,833 | 4/1992 | Broze, Jr. et al. | 514/12 |
| 5,212,091 | 5/1993 | Diaz-Collier et al. | 435/69.6 |
| 5,276,015 | 1/1994 | Khouri et al. | 514/12 |
| 5,563,123 | 10/1996 | Innis et al. | 514/12 |

OTHER PUBLICATIONS

Creasey et al, *J. Clin. Invest.* (1993) 91:2850–2860.
Idell, et al, *Am. Rev. Respire. Ids.* (1985) 132:1098.
Jochum, M., et al, *Am. J. Respire. Crate. Care Med.* (1994) 150:S123.
Petersen et al, *J. Biol. Chem.* (1993) 268(18):133344–13351.
Repine, *Lancet* (1992) 339:466–469.
Sprecher et al, *Proc. Nat. Acad. Sci., (USA)* (1994) 91:3353–3357.

*Primary Examiner*—Sheela Huff
*Assistant Examiner*—Yvonne Eyler
*Attorney, Agent, or Firm*—Banner & Witcoff; Sarah A. Kagan; Robert P. Blackburn

[57] ABSTRACT

Methods of treatment and prevention of diseases associated with release of neutrophil elastase and IL-8 by administration of TFPI, and analogs of TFPI are disclosed. Methods of determining efficacy of treatment with TFPI, patient's responsiveness to treatment with TFPI and the ultimate determination of patient prognosis are also disclosed.

5 Claims, 10 Drawing Sheets

REGULATION OF CYTOKINE SYNTHESIS AND RELEASE

TECHNICAL FIELD

The invention relates to the use of Tissue Factor Pathway Inhibitor (TFPI) to inhibit the synthesis and release of neutrophil elastase, IL-8 and plasmin.

BACKGROUND OF THE INVENTION

Tissue Factor Pathway Inhibitor (TFPI) inhibits the coagulation cascade in at least two ways: preventing formation of factor VIIa/tissue factor complex and by binding to the active site of factor Xa. The primary sequence of TFPI, deduced from cDNA sequence, indicates that the protein contains three Kunitz-type enzyme inhibitor domains. The first of these domains is required for the inhibition of the factor VIIa/tissue factor complex. The second Kunitz-type domain is needed for the inhibition of factor Xa. The function of the third Kunitz-type domain is unknown. TFPI has no known enzymatic activity and is thought to inhibit its protease targets in a stoichiometric manner; namely, binding of one TFPI Kunitz-type domain to the active site of one protease molecule. The carboxy-terminal end of TFPI is believed to have a role in cell surface localization via heparin binding and by interaction with phospholipid. TFPI is also known as Lipoprotein Associated Coagulation Inhibitor (LACI), Tissue Factor Inhibitor (TFI), and Extrinsic Pathway Inhibitor (EPI).

Mature TFPI is 276 amino acids in length with a negatively charged amino terminal end and a positively charged carboxy-terminal end. TFPI contains 18 cysteine residues and forms 9 disulphide bridges when correctly folded. The primary sequence also contains three Asn-X-Ser/Thr N-linked glycosylation consensus sites, the asparagine residues located at positions 145, 195 and 256. The carbohydrate component of mature TFPI is approximately 30% of the mass of the protein. However, data from proteolytic mapping and mass spectral data imply that the carbohydrate moieties are heterogeneous. TFPI is also found to be phosphorylated at the serine residue in position 2 of the protein to varying degrees. The phosphorylation does not appear to affect TFPI function.

TFPI has been isolated from human plasma and from human tissue culture cells including HepG2, Chang liver and SK hepatoma cells. Recombinant TFPI has been expressed in mouse C127 cells, baby hamster kidney cells, Chinese hamster ovary cells and human SK hepatoma cells. Recombinant TFPI from the mouse C127 cells has been shown in animal models to inhibit tissue-factor induced coagulation.

A non-glycosylated form of recombinant TFPI has been produced and isolated from *Escherichia coli* (*E. coli*) cells as disclosed in U.S. Pat. No. 5,212,091. This form of TFPI has been shown to be active in the inhibition of bovine factor Xa and in the inhibition of human tissue factor-induced coagulation in plasma. Methods have also been disclosed for purification of TFPI from yeast cell culture medium, such as in Petersen et al, *J.Biol.Chem.* 18:13344–13351 (1993).

Recently, another protein with a high degree of structural identity to TFPI has been identified. Sprecher et al, *Proc. Nat. Acad. Sci.*, USA 91:3353–3357 (1994). The predicted secondary structure of this protein, called TFPI-2, is virtually identical to TFPI with 3 Kunitz-type domains, 9 cysteine—cysteine linkages, an acidic amino terminus and a basic carboxy-terminal tail. The three Kunitz-type domains of TFPI-2 exhibit 43%, 35% and 53% primary sequence identity with TFPI Kunitz-type domains 1, 2, and 3, respectively. Recombinant TFPI-2 strongly inhibits the amidolytic activity of factor VIIa/tissue factor. By contrast, TFPI-2 is a weak inhibitor of factor Xa amidolytic activity.

TFPI has been shown to prevent mortality in a lethal *Escherichia coli* (*E. coli*) septic shock baboon model. Creasey et al, *J. Clin. Invest.* 91:2850–2860 (1993). Administration of TFPI at 6 mg/kg body weight shortly after infusion of a lethal dose of *E. coli* resulted in survival in all five TFPI-treated animals with significant improvement in quality of life compared with a mean survival time for the five control animals of 39.9 hours. The administration of TFPI also resulted in significant attenuation of the coagulation response, of various measures of cell injury and significant reduction in pathology normally observed in *E. coli* sepsis target organs, including kidneys, adrenal glands, and lungs.

Due to its clot-inhibiting properties, TFPI may also be used to prevent thrombosis during microvascular surgery. For example, U.S. Pat. No. 5,276,015 discloses the use of TFPI in a method for reducing thrombogenicity of microvascular anastomoses wherein TFPI is administered at the site of the microvascular anastomoses contemporaneously with microvascular reconstruction.

Neutrophil elastase release is linked to acute inflammatory diseases including ARDS and multiple organ failure. Idle, et al, (1985) Am. Rev. Respire. Ids. 132:1098. Joshua, M., et al, (1994) Am. J. Respire. Crate. Care Med. 150:S123. Acute inflammatory reactions, including ARDS, reperfusion injury (including lung reperfusion injury), arthritis, and sepsis are also associated with the production of cytokines such as IL-8. IL-8 is thought to play an important role in the recruitment and activation of PMNs at inflammatory sites.

Currently, there is no single agent which might effectively inhibit both thrombosis due to activation of the extrinsic pathway of coagulation and the release of inflammatory mediators such as neutrophil elastase.

SUMMARY OF THE INVENTION

It has now been found that coagulation activation and LPS (the active moiety of bacterial endotoxin) synergize for elastase release and that TFPI inhibits elastase release induced by coagulation activation and by coagulation in the presence of LPS. Further, TFPI has been shown to inhibit plasmin activity at therapeutically relevant doses. Therefore, TFPI has been shown to be relevant and is useful in disease states involving inflammation resulting from elastase release. Accordingly, TFPI may be used to treat such clinical indications as severe acute pancreatitis, emphysema, rheumatoid arthritis, multiple organ failure, cystic fibrosis, Adult Respiratory Distress Syndrome ('ARDS') and sepsis.

It has also been found coagulation activation/clotting induces IL-8 production in normal human whole blood cultures. Moreover, it has been found that coagulation activation/clotting and LPS together in whole blood cultures synergize for increased IL-8 production. TFPI is able to block the IL-8 production induced under both circumstances. Thus, TFPI may be used to treat such clinical indications as ARDS, reperfusion injury (including lung reperfusion injury), sepsis and arthritis.

Finally, the observation that TFPI inhibits the synthesis and release of neutrophil elastase, plasmin and IL-8 allow the use of assays for elastase, plasmin and IL-8 to be used to determine the patient's response to TFPI.

BRIEF DESCRIPTION OF THE DRAWINGS

FIG. 1 shows production of neutrophil elastase in undiluted whole blood cultures under the following conditions:

control (clot); TFPI (10 μg/ml); LPS (1 ng/ml)(clot); TFPI +LPS and heparin (50 u/ml).

DETAILED DESCRIPTION OF THE INVENTION

A. Definitions

As used herein, "TFPI" refers to mature Tissue Factor Pathway Inhibitor. As noted above, TFPI is also known in the art as Lipoprotein Associated Coagulation Inhibitor (LACI), Extrinsic Pathway Inhibitor (EPI) and Tissue Factor Inhibitor (or TFI). Muteins of TFPI which retain the biological activity of TFPI are encompassed in this definition. Further, TFPI which has been slightly modified for production in bacterial cells is encompassed in the definition as well. For example, a TFPI analog have an alanine residue at the amino-terminal end of the TFPI polypeptide has been produced in *Escherichia coli*. See U.S. Pat. No. 5,212,091. Analogs of TFPI having portions of TFPI and TFPI-2, fragments of TFPI comprising the first and second Kunitz-type domains, as well as fragments of TFPI comprising the first and second Kunitz domains and a heparin binding region may all be useful in the method of the invention. Such analogs and fragments are described in U.S. Pat. No. 5,106,833 as well as U.S. Ser. No. 08/286,521. One such fragment is TFPI(1–160) having the first 160 amino acids of mature TFPI.

As used herein, "pharmaceutically acceptable composition" refers to a composition that does not negate or reduce the biological activity of formulated TFPI, and that does not have any adverse biological effects when formulated TFPI is administered to a patient.

As used herein, "patient" encompasses human and veterinary patients.

B. General Methods

TFPI may be prepared by recombinant methods as disclosed in U.S. Pat. No. 5,212,091, the disclosure of which is herein incorporated by reference. Briefly, TFPI is expressed in *Escherichia coli* cells and the inclusion bodies containing TFPI are isolated from the rest of the cellular material. The inclusion bodies are subjected to sulfitolysis, purified using ion exchange chromatography, refolded by disulfide interchange reaction and the refolded, active TFPI purified by cation exchange chromatography. TFPI may also be produced in yeast as disclosed in co-pending U.S. Ser. No. 08/286,530.

Whole Blood Culture

The whole blood culture system can be carried out as follows. Blood is collected from normal donors into anticoagulant. Venous blood from normal health donors was collected directly into clinical heparin or EDTA (K3) vacutainers (Baxter). Alternatively, venous blood was collected into sterile polypropylene syringes and immediately transferred into microtiter wells containing indicated concentrations of various additives including:

a. 20–50 U/ml heparin (blood fully anticoagulated, even with 10X dilution)
b. 50–60 U/ml hirudin (recombinant yeast, American Diagnostica)
c. 10 μg/ml TFPI
d. 1 U/ml heparin (ESI)
e. 10 mM EDTA (for isolated neutrophils)
f. 1 ng/ml LPS (*E. coli* Rc) (Sigma, St. Louis, Mo.)
g. 3.8% citrate (for isolated PBMC).

TFPI was formulated at 11 mg/ml in 2M urea, 20 mM sodium phosphate pH 7.2 and 0.14M NaCl. Blood collected into vacutainers was quickly transferred into polypropylene tubes prior to addition into culture wells.

Whole blood was cultured in 96 well microtiter plates (Corning) at a volume of 200 μl per well at 37C, 5% $CO_2$ for 2–48 hours in a humidified atmosphere. The blood will typically be at a final dilution of 1:8 to 1:10 in RPMI 1640 medium +0.1% "low-endotoxin" fetal calf serum (FCS) (Hyclone, Logan, Utah). The cultures were then spun down at 400×g for 1 minute at 4° C. Supernatant liquids were then removed at various time points (typically 2–2.5 hours) for analysis of soluble mediators. In the event that clotting occurred during culturing, the contents of clotted wells and comparative groups were transferred to polypropylene microfuge tubes and briefly spun to pellet cells and fibrin clot prior to harvesting supernatants. Soluble mediators were measured in supernatants by ELISA or other bioassay.

Peripheral Blood Mononuclear Cell (PBMC) Cultures

Whole blood was collected into EDTA vacutainers was layered over a ficoll gradient (NIM medium, Cardinal Assoc.) at a mixture of 7–8 ml blood onto 5 ml NIM medium in 15 ml polystyrene tubes. The tubes were spun at 500×g for 30 minutes and the mononuclear cell layer was isolated as the top band in the gradient. In some experiments, PBMC were also isolated using citrated Cell Preparation Tubes (Becton-Dickinson, Mountain View, Calif.) wherein blood is collected and fractionated in the same tube. Identical results were obtain utilizing PBMC isolated in either manner. Following a sterile saline wash, PBMC were cultured at ~1×10$^5$ cells per well in RPMI/0.1% FCS as described above for whole blood cell cultures.

Assay for Soluble Mediators

ELISA assays for elastase, IL-8, IL-6 and TNF were conducted as follows. 96 well microtiter plates were coated overnight with the appropriate antibodies. Plates were washed and samples were added to each well along with biotin-labelled antibody and serum. The plates were then incubated and washed. Streptavidin-horseradish peroxidase was then added to the wells and allowed to incubate. The wells were again washed and developed with TMB, sodium acetate and peroxide. The reaction was stopped by the addition of 2M sulfuric acid and plates read at O.D. 450 nm. When assaying for elastase, there is an incubation period between the addition of the samples and the biotinylated anti-elastase antibodies. For TNF, poly-streptavidin-horseradish peroxidase and milk are used instead of Strep-HRP and serum.

Spectrozyme Plasmin assay kits were obtained from American Diagnostica. Quantikine IL-1β ELISA kits were purchased from R&D Systems. The manufacturers' instructions were followed in completing the assays.

Coagulation Activation

Measurement of the extent of coagulation activation was performed in a qualitative manner by observation of clotting and, quantitatively, via immunodetection of thrombin:antithrombin (TAT) complex and fibrinopeptide A levels according to manufacturer's protocols (Diagnostica Stago, France). Supernatants were also routinely analyzed for chromogenic activity against various substrates including Spectrozyme Xa and TH (thrombin)(American Diagnostica) for correlation with the above metrics as well as to confirm activity of purified factors added to isolated PBMC cultures including prothrombin, α-thrombin, and factor Xa.

C. Examples

EXAMPLE 1

A culture system utilizing normal human blood wherein coagulation activation and clotting could be controlled and inflammatory mediator responses could be evaluated in the presence or absence of LPS was established. Essentially, blood is collected in concentrations of anticoagulant, such as the irreversible thrombin inhibitor hirudin. When cultured at final blood dilutions of 1:10, coagulation activation and clotting could be observed. The extent of coagulation activation and clotting can be controlled by appropriate additions of anticoagulants upon blood dilution.

Figure 1:
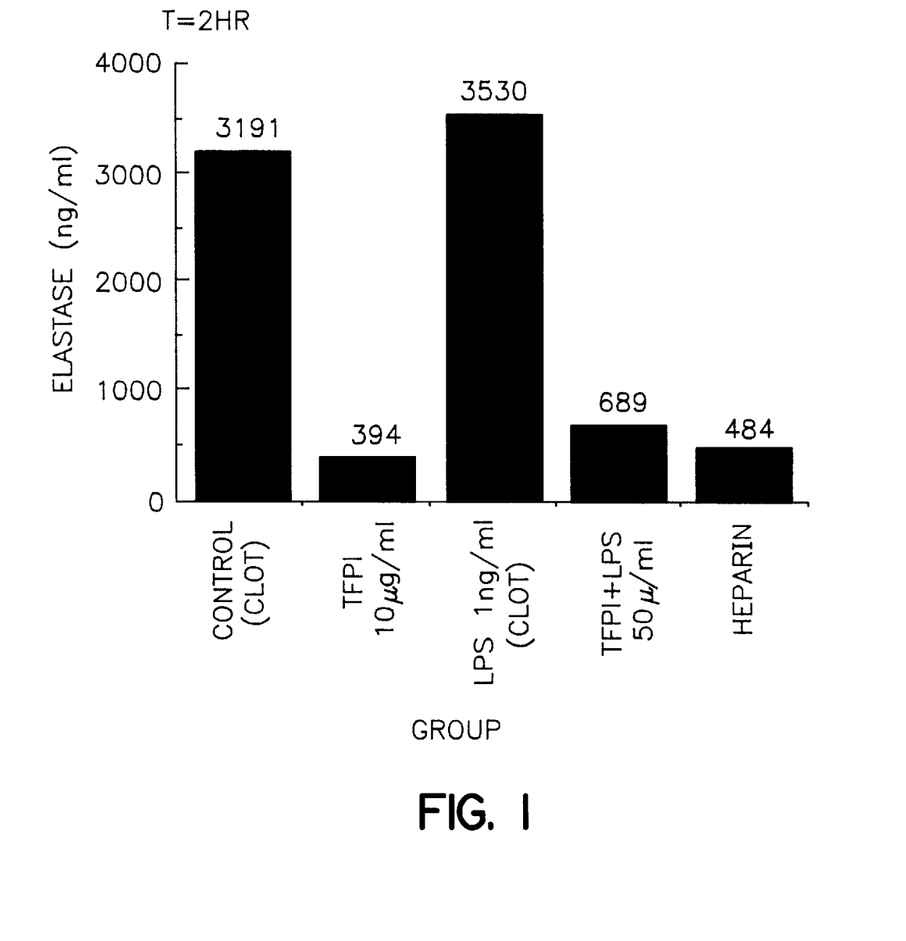

While most examinations of the effect of coagulation activation/clotting on elastase release have been performed in 1:10 diluted blood, the phenomena was observed in undiluted whole blood as indicated in FIG. 1. The incubation was carried out for two hours. Clotting the whole blood resulted in significant elastase release in the supernatant as compared to blood treated with 50 U/ml heparin. In undiluted whole blood, the addition of LPS resulted in only a small increment in elastase production, probably because the coagulation signal itself is so strong in the culture. TFPI addition at t=0 abrogates the coagulation and coagulation+LPS induced elastase release.

Figure 2:
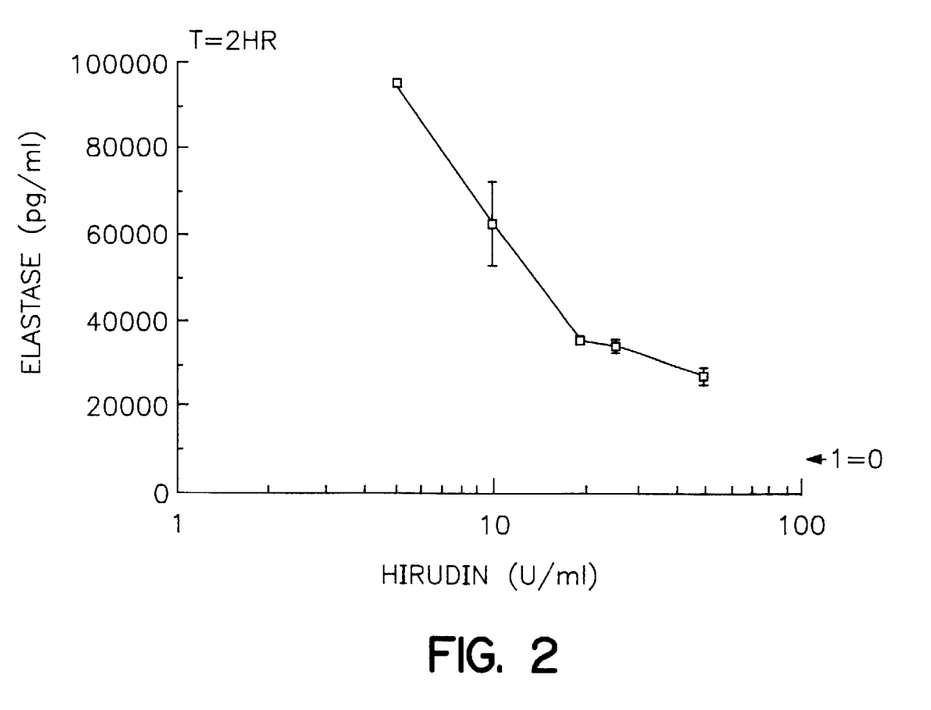
FIG. 2 shows production of neutrophil elastase in coagulating 1:10 whole blood culture containing various concentrations of hirudin.
Figure 3:
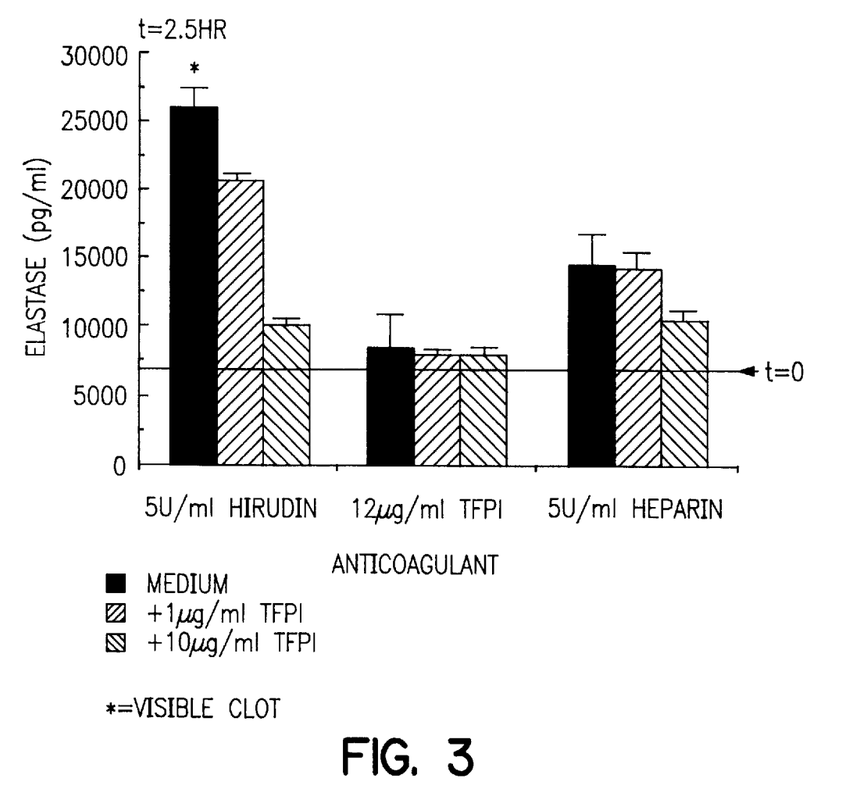
FIG. 3 shows production of neutrophil elastase in diluted (1:10) whole blood cultures containing various concentrations of TFPI and hirudin or heparin.
Figure 4:
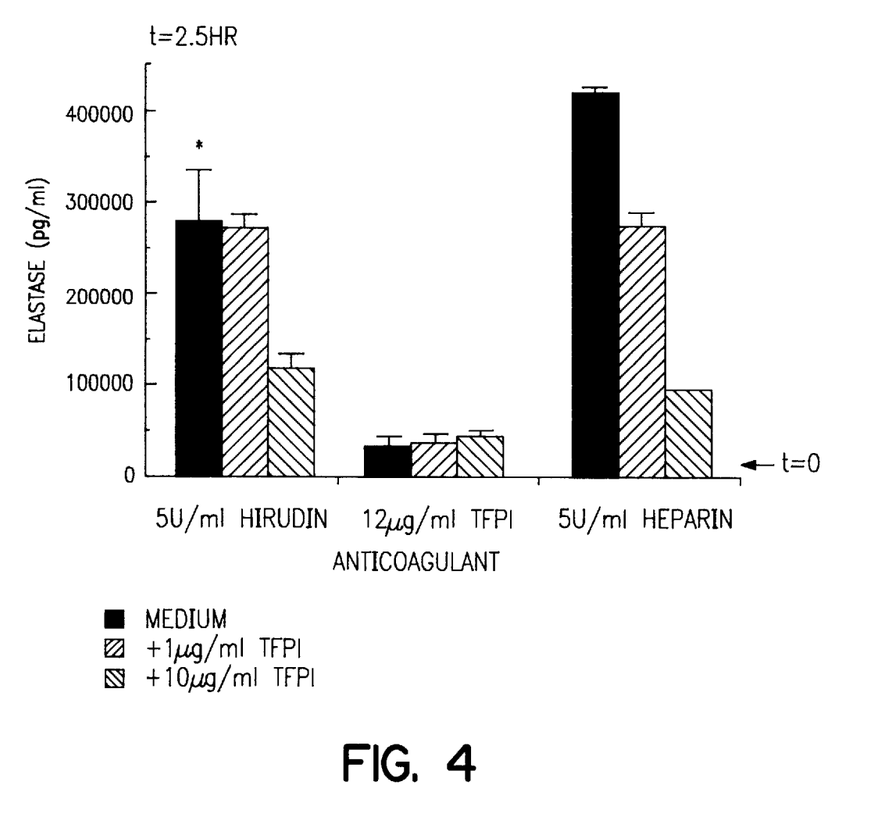
FIG. 4 shows production of neutrophil elastase in diluted (1:10) whole blood cultures containing 1 ng/ml LPS in addition to various concentrations of TFPI and hirudin or heparin.

As shown in FIG. 2, dilution of hirudin such that coagulation activation/clotting through thrombin can proceed is accompanied by elastase release which is most marked at low hirudin concentrations (5 & 10 U/ml) wherein clotting can be observed the time of harvest (t=2 hours). The addition of low concentrations of TFPI to hirudin-treated blood cultures (5 U/ml hirudin) blocks elastase release in a dose-dependent manner (FIG. 3). Addition of LPS in the low-hirudin culture results in significantly more elastase production (FIG. 4). Nonetheless, TFPI markedly inhibits the elastase released.

In contrast to anticoagulated blood collected in heparin, blood collected into TFPI fails to exhibit the synergistic elastase release observed upon culture with LPS. Moreover, the coagulation/LPS-induced elastase release in heparin-anticoagulated blood can be inhibited by the addition of TFPI to the culture at t=0 (FIG. 4).

Figure 5:
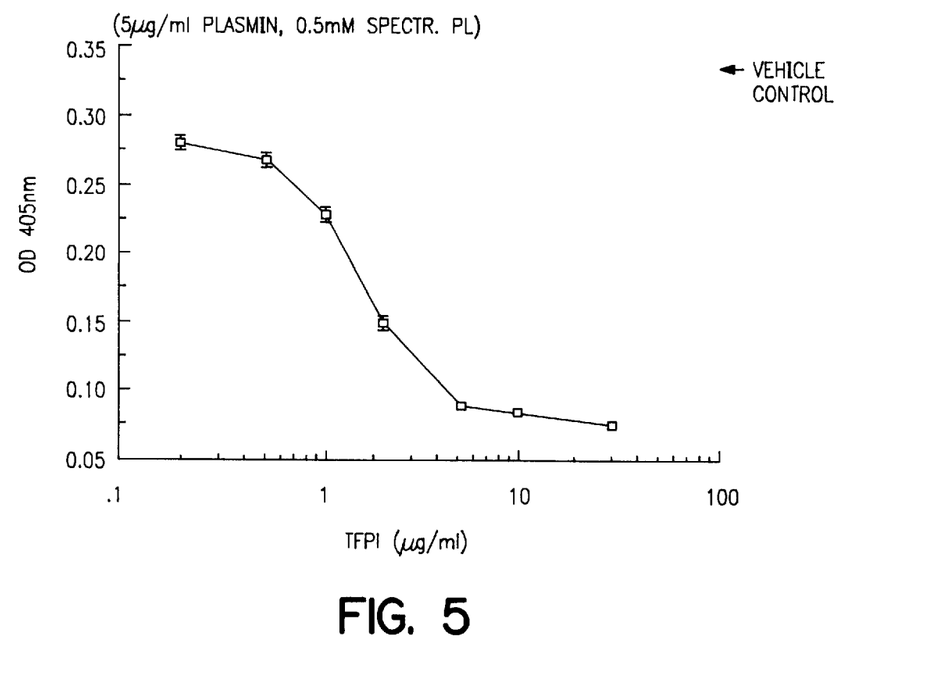
FIG. 5 displays the results of experiments showing that TFPI inhibits plasmin activity.

Finally, the effect of the presence of TFPI in the cultures on synthesis and release of plasmin was determined. FIG. 5 shows that increasing concentrations of TFPI result in decreased detection of plasmin activity in the cultures. The inhibitory effect of TFPI on plasmin activity may therefore serve as a marker for efficacy of TFPI in patients.

EXAMPLE 2

Using the culture system described above, it has been found that IL-8 production increases as a result of the coagulation activation/clotting. Also, coagulation activation/clotting and LPS appear to have a synergistic effect for IL-8 synthesis and release.

Figure 6:
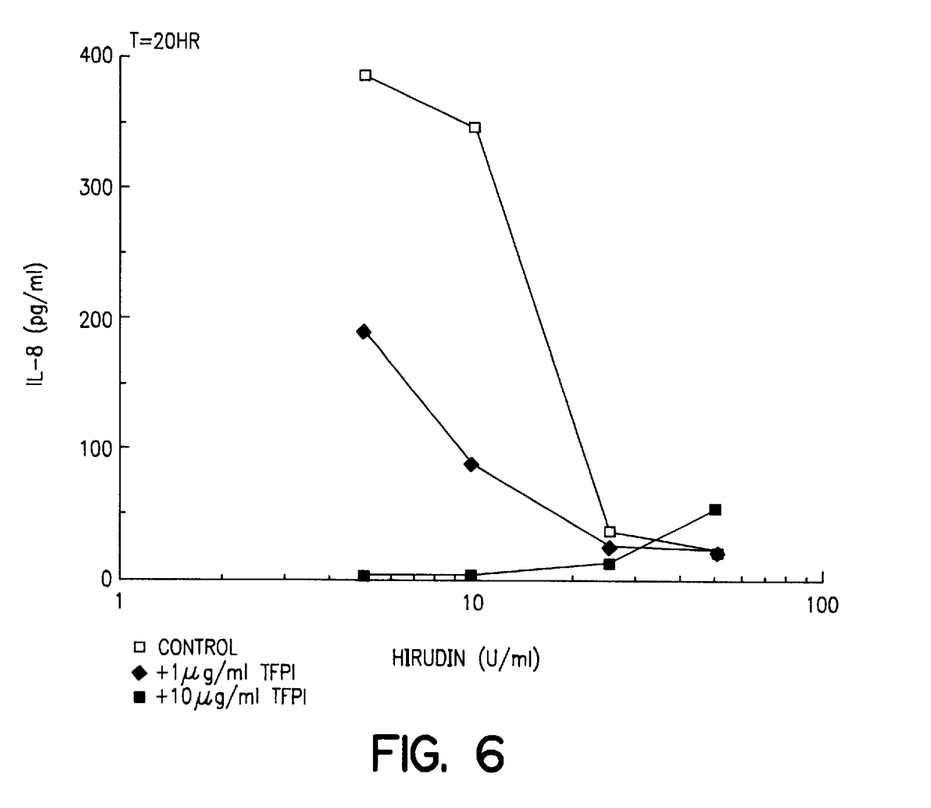
FIG. 6 displays the results of experiments showing that IL-8 levels in whole blood culture are drastically reduced in the presence of TFPI.

Dilution of hirudin in the blood cultures allows thrombin amplification of the coagulation cascade resulting in significant coagulation activation and observable clotting. Coincident with coagulation activation/clotting is the production of IL-8 into culture supernatants detectable by ELISA (FIG. 6). TFPI inhibits the coagulation activation/clotting-induce IL-8 production in a dose dependent manner (FIG. 6).

Figure 7:
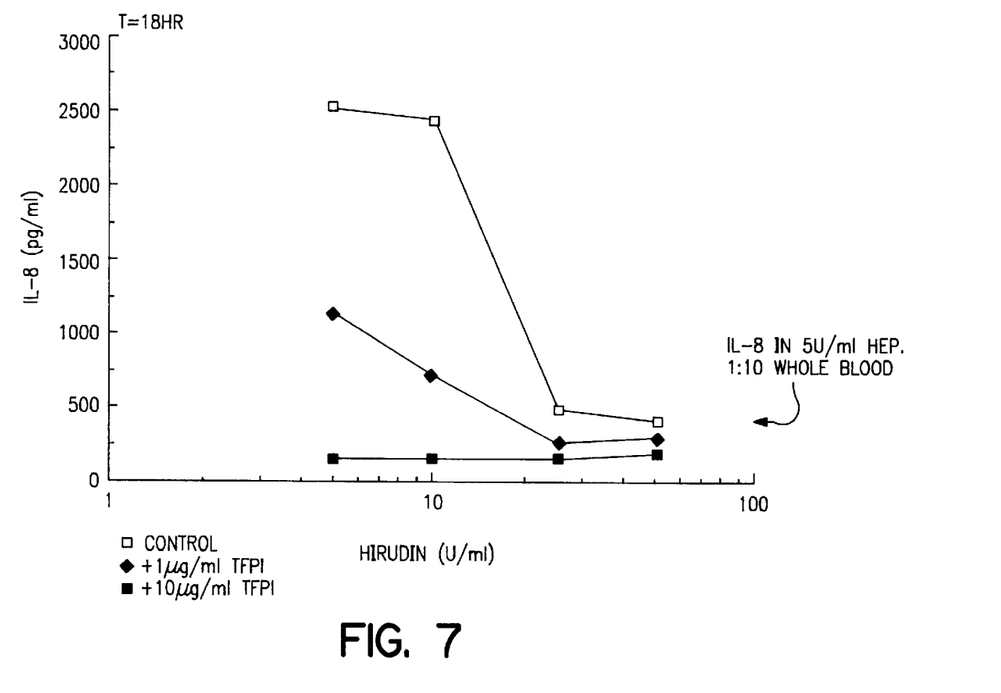
FIG. 7 shows the synergistic effect of coagulation activation/clotting and LPS in whole blood cultures on IL-8 levels.

When LPS (1 ng/ml) is included in the hirudin-treated blood cultures, a synergistic increase in IL-8 production is observed under conditions where significant coagulation activation/clotting occurs (i.e. 5–10 U/ml hirudin) (FIG. 7). The response is synergistic because coagulation activation/clotting results in ~350 pg/ml IL-8 and LPS induces ~450 pg/ml IL-8 under fully anticoagulated conditions (50 U/ml hirudin or 5 U/ml heparin), but the combinations of coagulation activation/clotting and LPS results in ~2500 pg/ml IL-8 production. As shown in FIG. 7, TFPI inhibits the synergistic IL-8 production in a dose-dependent manner.

Figure 8:
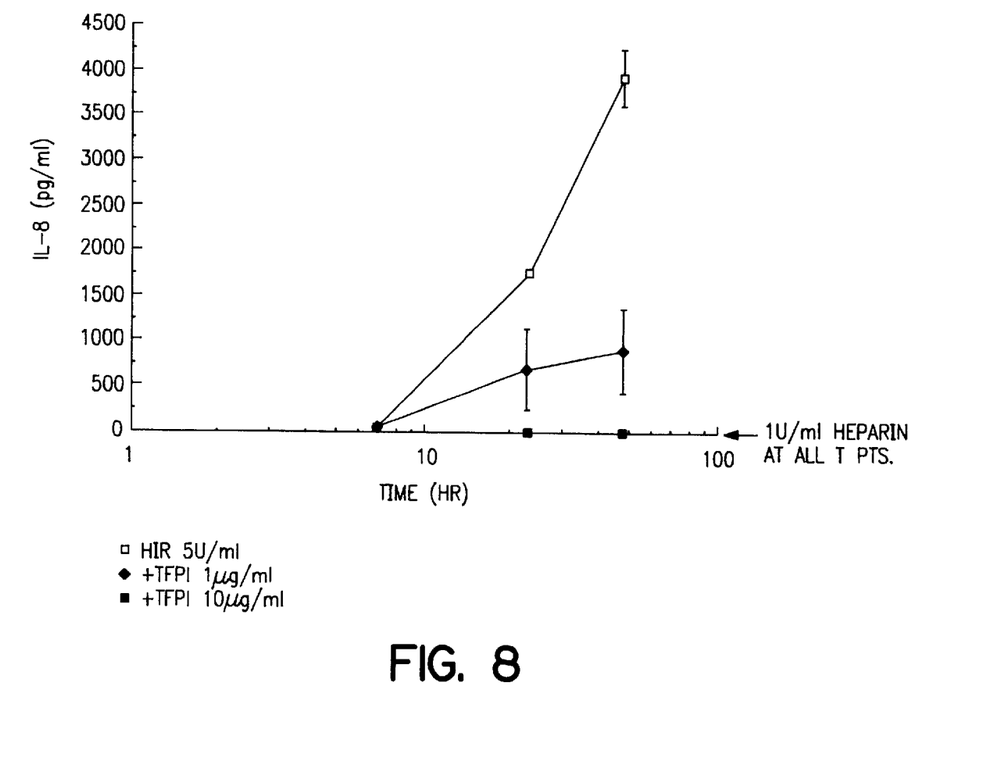
FIGS. 8 and 9 show the results of time course experiments measuring IL-8 levels in whole blood cultures in the absence (FIG. 8) and the presence (FIG. 9) of LPS.
Figure 9:
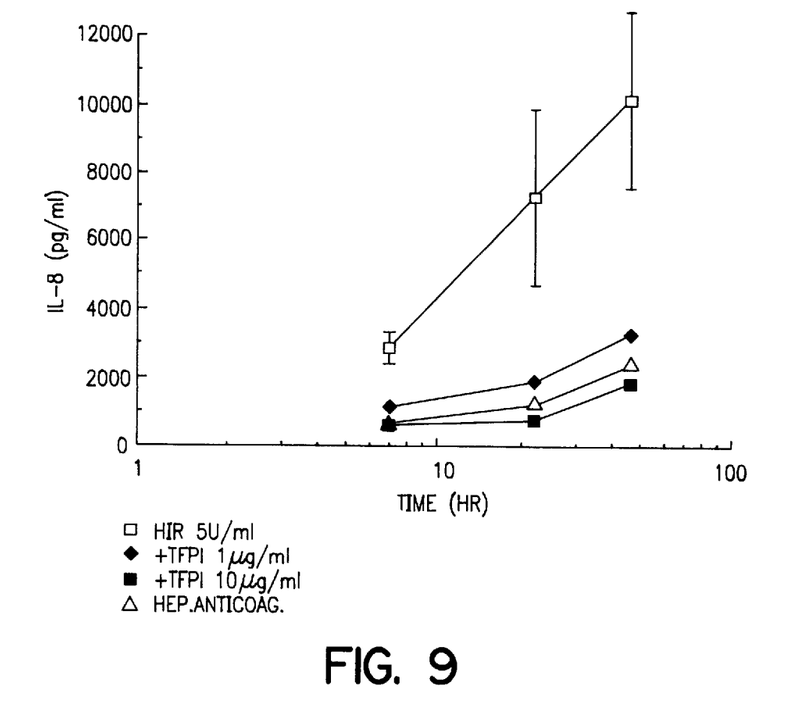

The ability of TFPI to abrogate IL-8 production induced by coagulation activation/clotting or the combination of coagulation activation/clotting+LPS is not due to altered kinetics of cytokine production (FIGS. 8 and 9). TFPI inhibits induced IL-8 production at all time points evaluated.

Figure 10:
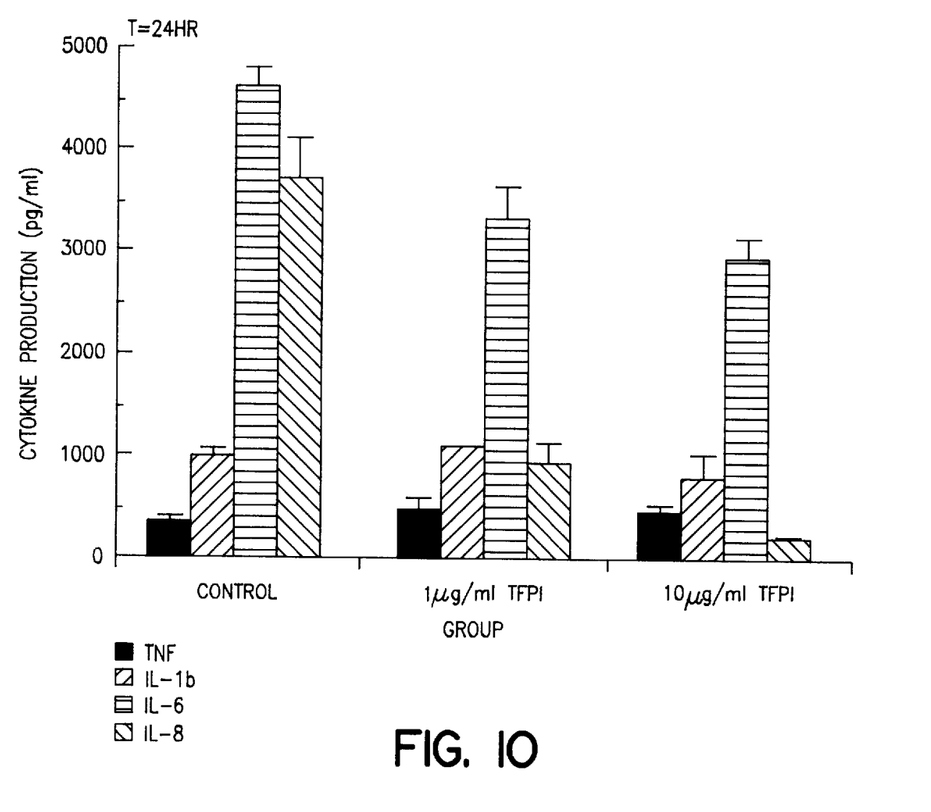
FIG. 10 shows the effect of TFPI on cytokine production in whole blood cultures containing 5 U/ml Hirudin and 1 ng/ml LPS.

The described IL-8 response to the combination of coagulation activation/clotting +LPS is somewhat unique as the combination does not result in synergistic production of TNFα, IL-6 or IL-1β (FIG. 10). Moreover, production of TNFα or IL-1β induced in low-hirudin+LPS cultures is not significantly inhibited by added TFPI concentrations to 10 µg/ml. While IL-6 production is slightly inhibited by TFPI, the IL-8 response is most significantly reduced by TFPI. The mechanism for the TFPI effect on induced IL-8 production in these cultures has not been determined. Without being bound to any particular theory, it may be that the ability of TFPI to inhibit coagulation activation by direct inhibition of factor Xa and the inhibition of factor VIIa/tissue factor in a Xa-dependent manner. However, it may be that TFPI has some ability to directly inhibit LPS activity.

EXAMPLE 3

Adult Respiratory Distress Syndrome (ARDS) is an acute inflammatory process characterized by neutrophil accumulation and edema in the lungs, as well as progressive hypoxemia. Repine, (1992) Lancet 339:466–469. ARDS is an inflammatory disease occurring as a complicating factor in a number of diseases including sepsis. Patients diagnosed with ARDS can be treated by administration of an effective amount of TFPI. The dosage of TFPI will vary according to a number of factors including progress of ARDS (soon after onset to late stage disease), patient size and other factors known to and appreciated by those skilled in the art.

Patients at risk for developing ARDS may be identified by chest X-ray. Opaqueness of the radiogram lung area is indicative of neutrophil migration into the lung and is an accepted clinical diagnostic hallmark of ARDS.

EXAMPLE 4

The inhibitory effect of TFPI on the synthesis and release of neutrophil elastase, IL-8 and on plasmin may be used to assess the efficacy of treatment in patients with thrombosis disorders, patients with diseases associated with increased neutrophil elastase and in patients with diseases associated with increased IL-8. It is believed that the levels of neutrophil elastase, IL-8 and plasmin may be predictive of patient responsiveness to TFPI and prognosis. Patients who have received TFPI will have blood drawn and assayed for neutrophil elastase levels, for IL-8 levels, for plasmin activity or for any combination of these indicators. Levels for each of these indicators may be compared to an established historical baseline, as determined by sampling of populations of normal human volunteers. Alternatively, the level of neutrophil elastase, IL-8 or plasmin per patient may be followed over time prior to and after administration of TFPI. In the event that levels of the indicator or indicators tested have not decreased, additional dosing with TFPI may be required.

We claim:

1. A method for measuring a patient's response to Tissue Factor Pathway Inhibitor (TFPI), comprising the step of determining the level of one or more indicators selected from the group consisting of neutrophil elastase, interleukin-8 and plasmin, wherein a decrease in the level of neutrophil elastase, interleukin-8, or plasmin indicates a response of the patient to TFPI.

2. The method of claim 1 wherein the levels of neutrophil elastase, interleukin-8, and plasmin are determined.

3. The method of claim 1 wherein the patient has been diagnosed with one or more diseases associated with increased synthesis and release of neutrophil elastase
selected from the group consisting of severe acute pancreatitis,
emphysema,
rheumatoid arthritis,
multiple organ failure,
cystic fibrosis,
sepsis, and
Adult Respiratory Distress Syndrome.

4. The method of claim 1 wherein the patient has been diagnosed with one or more diseases associated with increased synthesis and release of interleukin-8 selected from the group consisting of
Adult Respiratory Distress Syndrome, reperfusion injury,
sepsis, and
arthritis.

5. The method of claim 1 wherein the patient has been diagnosed with a thrombosis related syndrome.

\* \* \* \* \*